US009909976B2

(12) United States Patent
Krishnamachari

(10) Patent No.: US 9,909,976 B2
(45) Date of Patent: Mar. 6, 2018

(54) SCANNING MICROSCOPE WITH POLARISED SAMPLE ILLUMINATION

(71) Applicant: LEICA MICROSYSTEMS CMS GMBH, Wetzlar (DE)

(72) Inventor: Vishnu Vardhan Krishnamachari, Seeheim-Jugenheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 79 days.

(21) Appl. No.: 14/916,538

(22) PCT Filed: Sep. 3, 2014

(86) PCT No.: PCT/EP2014/068751
§ 371 (c)(1),
(2) Date: Mar. 3, 2016

(87) PCT Pub. No.: WO2015/032823
PCT Pub. Date: Mar. 12, 2015

(65) Prior Publication Data
US 2016/0223457 A1 Aug. 4, 2016

(30) Foreign Application Priority Data

Sep. 3, 2013 (DE) .................. 10 2013 217 499
Dec. 23, 2013 (DE) .................. 10 2013 227 108

(51) Int. Cl.
*G01J 3/44* (2006.01)
*G01N 21/21* (2006.01)
(Continued)

(52) U.S. Cl.
CPC ............ *G01N 21/21* (2013.01); *G01N 21/65* (2013.01); *G02B 21/002* (2013.01);
(Continued)

(58) Field of Classification Search
CPC .. G01N 21/21; G01N 21/65; G01N 2201/067; G01N 2201/0683;
(Continued)

(56) References Cited

U.S. PATENT DOCUMENTS 3,644,018 A * 2/1972 Pasold ................ G02B 5/3083
359/249
6,462,345 B1 10/2002 Simon et al.
(Continued)

OTHER PUBLICATIONS

Thomas J Fellers: "Olympus Fluoview Resource Center: Acousto-Optic Tunable Filters", Mar. 19, 2013, https://web.archive.org/web/20130319085942/http://www.olympusconfocal.com/theory/aotfin.tro.html.

*Primary Examiner* — Hina F Ayub
(74) *Attorney, Agent, or Firm* — Hodgson Russ LLP

(57) ABSTRACT

The invention relates to a method for investigating a sample, the sample being impinged upon by illuminating light, and detected light emerging from the sample being directed to a detector, and the illuminating light being directed through an acousto-optic component with which the impingement upon the sample by illuminating light can be temporarily interrupted. The method is notable for the fact that the sample is illuminated with a first illuminating light bundle that has a first linear polarization direction, and with a second illuminating light bundle whose linear polarization direction is continuously switched over between the first linear polarization direction and a second linear polarization direction different from the first linear polarization direction, the illuminating light having the first linear polarization direction proceeding along a first light path and illuminating light having the second linear polarization direction proceeding along a second light path, and the acousto-optic component combining the light paths.

33 Claims, 2 Drawing Sheets

Figure 1:
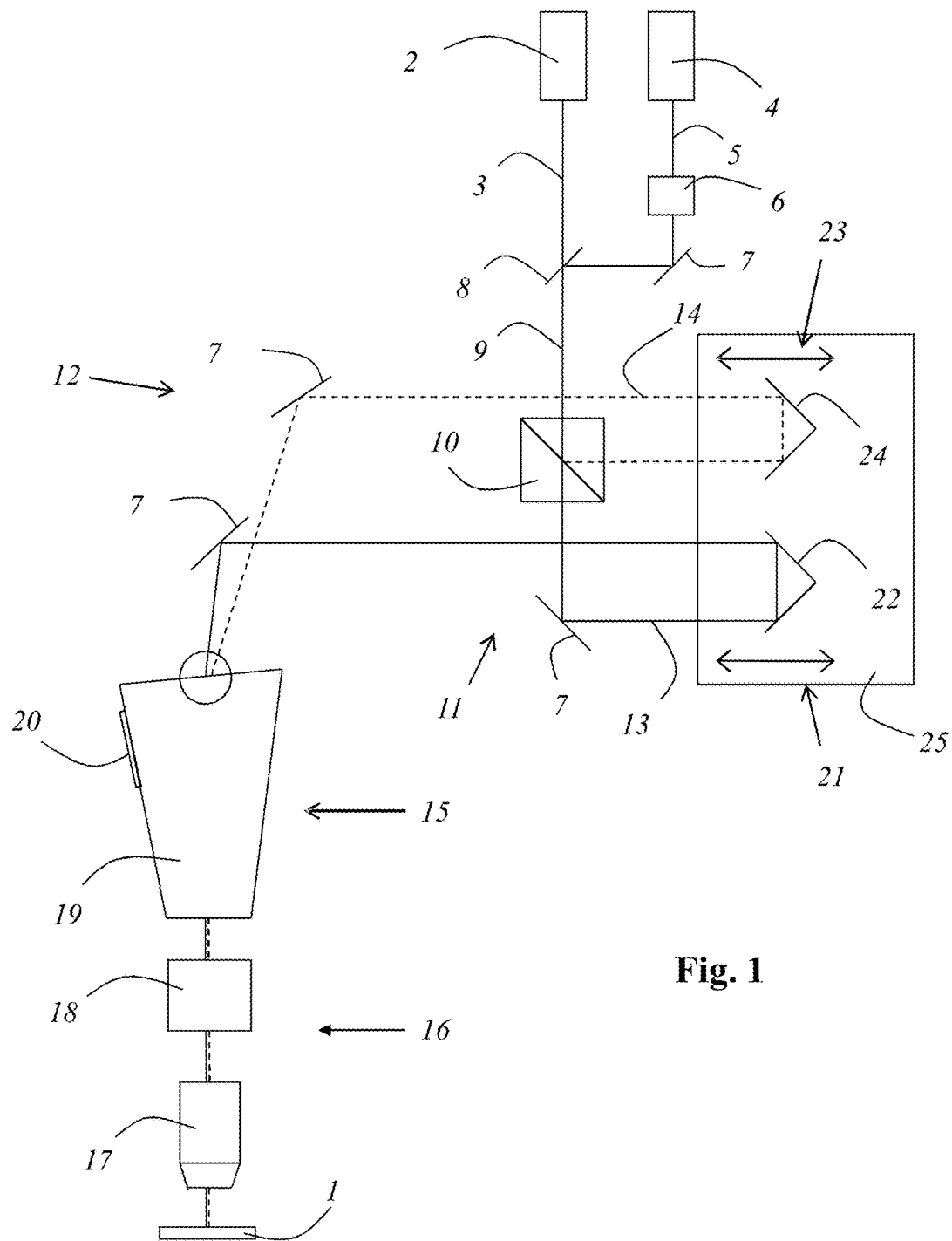

(51) Int. Cl.
    *G02B 21/00*     (2006.01)
    *G02B 27/28*     (2006.01)
    *G01N 21/65*     (2006.01)
(52) U.S. Cl.
    CPC ..... *G02B 21/0032* (2013.01); *G02B 21/0068* (2013.01); *G02B 27/283* (2013.01); *G02B 27/286* (2013.01); *G01N 2201/067* (2013.01); *G01N 2201/0683* (2013.01)
(58) Field of Classification Search
    CPC .............. G02B 21/002; G02B 21/0032; G02B 21/0068; G02B 27/283; G02B 27/286
    USPC ....................................................... 356/301
    See application file for complete search history.

(56) References Cited

U.S. PATENT DOCUMENTS

| | | | |
|---|---|---|---|
| 7,660,035 B2 | 2/2010 | Böhm et al. | |
| 8,259,383 B2 | 9/2012 | Seyfried | |
| 2001/0028031 A1 | 10/2001 | Engelhardt et al. | |
| 2004/0239929 A1* | 12/2004 | Boehm | G01J 3/14 |
| | | | 356/327 |
| 2013/0182306 A1* | 7/2013 | Anhut | G02B 21/0032 |
| | | | 359/246 |

\* cited by examiner

SCANNING MICROSCOPE WITH POLARISED SAMPLE ILLUMINATION

The invention relates to a method for investigating a sample, the sample being impinged upon by illuminating light, and detected light emerging from the sample being directed to a detector, and the illuminating light being directed through an acousto-optic component with which the impingement upon the sample by illuminating light can be temporarily interrupted.

The invention furthermore relates to an apparatus, in particular to a scanning microscope or confocal scanning microscope, for carrying out such a method, and to an apparatus, in particular to a scanning microscope or confocal scanning microscope, for investigating a sample, the sample being impinged upon by illuminating light, and detected light emerging from the sample being directed to a detector, and the illuminating light being directed through an acousto-optic component with which the impingement upon the sample by illuminating light can be temporarily interrupted.

The invention moreover relates to a module for manufacturing an apparatus according to the present invention.

In a microscope, in particular in a scanning microscope or a confocal scanning microscope, samples are often illuminated with an illuminating light bundle that has been generated by combining multiple illuminating light bundles, in order to observe the reflected or fluorescent light emitted from the illuminated sample.

In scanning microscopy, for example, the focus of an illuminating light beam of this kind is moved in a specimen plane with the aid of a controllable beam deflection device, generally by tilting two mirrors; the deflection axes are usually perpendicular to one another, so that one mirror deflects in an X direction and the other in a Y direction. Tilting of the mirrors is brought about, for example, with the aid of galvanometer positioning elements. The power level of the light coming from the specimen is measured as a function of the position of the scanning beam. The positioning elements are usually equipped with sensors for ascertaining the current mirror position.

In confocal scanning microscopy in particular, a specimen is scanned in three dimensions with the focus of an illuminating light bundle. A confocal scanning microscope generally encompasses a light source, a focusing optical system with which the light of the source is focused onto an aperture (called the "excitation pinhole"), a beam splitter, a beam deflection device for beam control, a microscope optical system, a detection pinhole, and the detectors for detecting the detected light or fluorescent light. The illuminating light is coupled in, for example, via a beam splitter.

The fluorescent light coming from the specimen travels via the beam deflection device back to the beam splitter, passes through the latter, and is then focused onto the detection pinhole behind which the detectors are located. Detected light that does not derive directly from the focus region takes a different light path and does not pass through the detection pinhole, so that a spot information item is obtained. A three-dimensional image can be generated by sequential scanning of the specimen.

The field of coherent Raman microscope (CRM) has for some time been very important and useful for image-producing investigation of biological and pharmacological samples, and in the sector of nutrition science. The advantage of coherent Raman microscopy as compared with conventional Raman microscopy is, in particular, the higher imaging speed.

Coherent anti-Stokes Raman scattering (CARS), coherent Stokes Raman scattering (CSRS), Raman-induced Kerr effect scattering (RIKES), and stimulated Raman scattering (SRS) represent a variety of CRM techniques. Among them, stimulated Raman scattering (SRS) has the particular advantage that the non-resonant background signals can be completely blocked out, and a higher signal to noise ratio is made possible.

The technique of stimulated Raman scattering (SRS) is based on directing two pulsed optical fields (having frequencies in the range from 40 to 100 MHz) having different wavelengths through a confocal microscope system onto a sample to be investigated. Suitable beam guidance and focusing ensure, in this context, that the two optical fields overlap spatially and temporally in the sample.

One of the two optical fields is either intensity-modulated or frequency-modulated or polarization-modulated, at a frequency $\Omega$ typically in the kHz to MHz range, before it interacts in the sample with the other optical field. After passage through the sample or reflection at the sample, the second optical field, which originally was not modulated, is detected, and the modulation amplitude thereof having the frequency $\Omega$ is measured. The modulation amplitude represents the SRS signal. The optical field having the higher wavelength can be, for example, a so-called "Stokes" illuminating light bundle, while the optical field having the lower wavelength can be referred to as a "pump" illuminating light bundle.

It is possible, for example, to modulate the Stokes illuminating light bundle and to detect the pump illuminating light bundle after a sample interaction. In this case the resulting signal is referred to as "stimulated Raman loss" (SRL). In the other case, namely when originally the pump illuminating light bundle is modulated, the Stokes illuminating light bundle is then detected after a sample interaction and the resulting signal is referred to as "stimulated Raman gain" (SRG). Both SRL and SRG are popular SRS methods; the information content of the signals is almost identical for the two methods. Among the various modulation methods for generating SRS images, intensity modulation is the simplest and most robust technique.

A practical problem that exists with SRS methods in which one of the optical fields is intensity-modulated, however, is that exclusively very thin samples can be used. The reason for this is that the very strong optical fields in the focal volume influence the refractive index of the sample. This effect is referred to as the "Kerr effect."

Modulation of one of the aforementioned optical fields therefore also results in a modulation of the refractive index of the sample, which entails various secondary effects such as self-phase modulation and formation of a Kerr lens that changes over time.

This results in a time-related modulation of the divergence of the optical field that emerges from the sample and is to be detected. If the numerical aperture of the collection optic is smaller than the numerical aperture of the focusing optic that is focusing the illuminating light, a temporally fluctuating portion of the detected light emerging from the sample is not captured by the collection optic. The modulation of the divergence of the detected light bundle is consequently perceived by the detector as an intensity modulation that is overlaid (in fact at the same modulation frequency) on the SRS signal that one would actually like to detect. This results in an obtrusive signal background.

In order to overcome this effect, collection optics having a large numerical aperture are used. This greatly limits, however, the sample thickness that can be used in the context of high-resolution SRS imaging. Thin sample disks having a thickness of a few tens of micrometers must be used for this. The consequences of these phenomena are long sample preparation times and limitations on the use of the image-producing method for high-resolution live cell imaging.

These disadvantages do not exist either with frequency-modulated SRS (FM-SRS) or with polarization-modulated SRS (PM-SRS). Implementation of a robust FM-SRS is, however, technically very complex.

Even with polarization-modulated SRS, however, there exists the very obtrusive practical problem that this technology is impossible to implement with an (in particular, confocal) scanning microscope whose illuminating light is adjusted in terms of light power level with the aid of one or more AOTFs, or whose illumination is temporarily shut off with the aid of one or more AOTFs, since the AOTF of a scanning microscope of this kind, as known e.g. from DE 198 29 981 A1, acts only on illuminating light having one wavelength and a specific polarization.

The object of the present invention is therefore to describe a method that allows implementation of coherent Raman microscopy using a scanning microscope, with which a temporary interruption of the illumination, and/or an adjustment of the light power level of the illumination, is possible.

The object is achieved by a method which is characterized in that the sample is illuminated with a first illuminating light bundle that has a first linear polarization direction, and with a second illuminating light bundle whose linear polarization direction is continuously switched over between the first linear polarization direction and a second linear polarization direction different from the first linear polarization direction, the illuminating light having the first linear polarization direction proceeding along a first light path and illuminating light having the second linear polarization direction proceeding along a second light path, and the acousto-optic component combining the light paths so that the illuminating light having the first linear polarization direction, combined collinearly with the illuminating light having the second linear polarization direction, travels into a common illumination beam path for illumination of the sample.

A further object of the present invention is to describe an apparatus, in particular a scanning microscope or confocal scanning microscope, that makes possible both a temporary interruption of the illumination and/or an adjustment of the light power level of the illumination, and allows a sample investigation to be carried out on the basis of coherent Raman spectroscopy.

The further object is achieved by an apparatus, in particular a scanning microscope or confocal scanning microscope, which is characterized in that the illuminating light comprises a first illuminating light bundle having a first linear polarization direction, and comprises a second illuminating light bundle whose linear polarization direction is continuously switched over by a switchover apparatus, in particular by an acousto-optic or electro-optic modulator, between the first linear polarization direction and a second linear polarization direction different from the first linear polarization direction, the illuminating light having the first linear polarization direction proceeding along a first light path and illuminating light having the second linear polarization direction proceeding along a second light path, and the acousto-optic component combining the light paths so that the illuminating light having the first linear polarization direction, combined collinearly with the illuminating light having the second linear polarization direction, travels into a common illumination beam path for illumination of the sample.

An additional object of the present invention is to describe a capability that makes it possible, quickly and efficiently, to manufacture an apparatus for carrying out a sample investigation on the basis of coherent Raman spectroscopy, which also permits temporary interruption of the illumination, or to permit an existing apparatus to be refitted therefor.

This object is achieved by a module which is characterized in that the module comprises a polarizing beam splitter that defines the beginning of a first and of a second light path, and an acousto-optic component that combines the first and the second light path.

The invention has the advantage that the first and/or the second illuminating light bundle can, for example, quickly be interrupted or enabled again. The possibility of rapid switchover to other wavelengths or other wavelength combinations is also advantageously provided. It is possible in particular to exploit the fact that the acousto-optic component can usually be switched within a few microseconds.

It is also possible according to the present invention to adjust and/or regulate the light power level of the first and/or of the second illuminating light bundle with the acousto-optic component.

The invention has the very particular advantage that the impingement upon a sample by the first illuminating light bundle and/or by the second illuminating light bundle can be temporarily interrupted with the aid of the acousto-optic component. In particular, unnecessary stress on the sample and thus, for example, premature bleaching of the sample can thereby effectively be prevented. Provision can be made, for example, that the acousto-optic component enables the light path to the sample, in particular in automatically controlled fashion, only when a detection of the illuminating light is occurring or when it is necessary in advance of an investigation, for example for a preview image.

Provision can advantageously be made, in particular, that the impingement upon a sample by the first illuminating light bundle and/or by the second illuminating light bundle is interrupted with the acousto-optic component, in particular automatically, if the first illuminating light bundle and/or the second illuminating light bundle would illuminate a region of the sample that is located outside a region to be investigated. Alternatively or additionally, provision can also be made that the impingement upon a sample by the first illuminating light bundle and/or by the second illuminating light bundle is interrupted with the acousto-optic component, in particular automatically, in the turnaround regions of a meander-shaped scan and/or on the return paths of an (in particular, meander-shaped) scan.

Provision can be made in particular that at least one mechanical wave, at which at least one of the illuminating light bundles is diffracted and is thereby directed into the illumination beam path for illumination of the sample, propagates in the acousto-optic component.

The invention furthermore has the very particular advantage that an investigation of a sample is made possible even with the use of collection optics that do not have a large numerical aperture, since the problems described previously, in particular a fluctuation over time in the divergence of the detected light, do not occur with the approach according to the present invention. It is therefore possible, in particularly advantageous fashion, also to investigate samples that have a substantially greater thickness than the samples that could hitherto be investigated.

In a particularly advantageous embodiment a first mechanical wave, whose frequency is selected so that the first illuminating light bundle is diffracted at it and is thereby directed into the illuminating light beam path for illumination of the sample, propagates in the acousto-optic component. Alternatively or additionally, provision can be made that a second mechanical wave, whose frequency is selected so that the second illuminating light bundle is diffracted at it and is thereby directed into the illuminating light beam path for illumination of the sample if said bundle has the first linear polarization direction, propagates in the acousto-optic component.

Alternatively or additionally, it is advantageously also possible for a third mechanical wave, whose frequency is selected so that the second illuminating light bundle is diffracted at it and is thereby directed into the illumination beam path for illumination of the sample if said bundle has the second linear polarization direction, to propagate in the acousto-optic component.

In particular, provision can advantageously be made that the acousto-optic component comprises at least one acousto-optic tunable filter (AOTF) in which the mechanical wave or mechanical waves propagate.

The manner of operation of an acousto-optic component of this kind is based substantially on the interaction of the incoupled illuminating light bundle with a mechanical wave or with multiple mechanical waves. Acousto-optic components are generally made up of a so-called acousto-optic crystal, on which is mounted an electrical converter (often referred to in the literature as a "transducer"). The converter preferably encompasses a piezoelectric material as well as one electrode located above it and one located below it. Electrical activation of the electrodes with radio frequencies, which are typically in the region between 30 MHz and 800 MHz, causes the piezoelectric material to vibrate, so that an acoustic wave (i.e. a sound wave) can occur and, once produced, passes through the crystal. After passing through an optical interaction region, the acoustic wave is usually absorbed or reflected away at the oppositely located side of the crystal.

Acousto-optic crystals are notable for the fact that the resulting sound wave modifies the optical properties of the crystal, a kind of optical grating or comparable optically active structure, for example a hologram, being induced by the sound. Light passing through the crystal experiences a diffraction at the optical grating. The light is correspondingly directed into various diffraction orders in diffraction directions. There are acousto-optic components that influence all of the incident light more or less irrespective of wavelength. Reference may be made, solely by way of example, to components such AOMs, AODs, and frequency shifters. Components moreover also already exist that, for example, act selectively on individual wavelengths as a function of the irradiated radio frequency (AOTFs). The acousto-optic elements are often made of birefringent crystals, for example tellurium oxide; the optical effect of the respective element is determined in particular by the location of the crystal axis relative to the incidence direction of the light and its polarization.

Especially when, for example, an AOTF is used in the acousto-optic beam combiner, the mechanical wave must have a very specific frequency so that the Bragg condition is exactly satisfied for the light having the desired illuminating light wavelength and the desired polarization. With these acousto-optic components, light for which the Bragg condition is not satisfied is not deflected by the mechanical wave.

Provision can be made in particular that the first linear polarization direction is the linear polarization direction of the ordinary light with respect to a birefringence property of the crystal; and/or that the second linear polarization direction is the linear polarization direction of the extraordinary light with respect to a birefringence property of the crystal; or conversely, provision can be made (alternatively or additionally) that that the first linear polarization direction or the second linear polarization direction is arranged in the plane that is spanned by the propagation direction of the mechanical wave and the propagation direction of the incident light bundle.

In a particular embodiment of the invention, firstly a primary illuminating light bundle, which contains the first illuminating light bundle and/or the second illuminating light bundle in collinearly combined fashion, is generated. A primary illuminating light bundle of this kind can be generated, for example, by combining the first illuminating light bundle with the second illuminating light bundle, the second illuminating light bundle having traversed, prior to combination, a light path spatially separate from the first illuminating light bundle, in which an element for switching over the linear polarization direction, for example an electro-optic or acousto-optic modulator, is arranged.

The primary illuminating light bundle is then spatially divided as a function of linear polarization, in particular with a polarizing beam splitter, and the portions having different linear polarizations are directed separately from one another into the first and second light path. This procedure has the advantage that the illuminating light having the first linear polarization direction can be coupled into a first input of the acousto-optic component while the illuminating light having the second linear polarization direction can be coupled into a second input, different and in particular spatially separated from the first input, of the acousto-optic component.

In particular, the portions having different linear polarizations can be coupled in so that at least one mechanical wave respectively acts on one of the portions, with the result that the portions are deflected, by diffraction, into a common illumination beam path in which the portions proceed in collinearly combined fashion.

For the acquisition of two-dimensional or three-dimensional image data, provision can be made that at least a partial region of the sample is scanned with the first illuminating light bundle and with the second illuminating light bundle, and/or that the foci of the first illuminating light bundle and of the second illuminating light bundle are moved collectively, with the aid of a beam deflection device, over or through the sample, and in that context the detected light emerging from the sample is detected. Collective deflection of the collinearly combined illuminating light bundles ensures that the foci of the illuminating light bundles spatially overlap in the sample.

In a very particularly advantageous embodiment, at least one of the illuminating light bundles, i.e. either the first illuminating light bundle and/or the second illuminating light bundle, is pulsed. Provision can be made in particular that the first illuminating light bundle and the second illuminating light bundle are pulsed at the same pulse repetition frequency. This is necessary in particular if the first illuminating light pulses and the second illuminating light pulses are intended to overlap temporally in the sample.

The pulse repetition frequency of the first illuminating light bundle and/or the pulse repetition frequency of the second illuminating light bundle is preferably in the range from 40 MHz to 100 MHz, in particular is 80 MHz.

The apparatus according to the present invention can comprise, for example, at least one light source that generates a primary illuminating light bundle that contains the first illuminating light bundle and/or the second illuminating light bundle. The first illuminating light bundle and/or the second illuminating light bundle can be generated, for example, with the aid of a mode-coupled pulsed laser. A pulsed laser of this kind can be followed (at least for one of the illuminating light bundles) by an element for influencing wavelength. It is also possible for the first illuminating light bundle and/or the second illuminating light bundle to derive from a so-called photonic fiber or a so-called tapered fiber that is part of a white light source.

In particular to ensure temporal superposition of the pulses in the sample, provision is made in a very particularly advantageous embodiment that the illuminating light having the first linear polarization direction, which proceeds along the first light path, comprises a train of first illuminating light pulses; and that the illuminating light having the second linear polarization direction, which proceeds along the second light path, comprises a train of second illuminating light pulses, the phase of the train of first illuminating light pulses relative to the train of second illuminating light pulses being adjusted and/or regulated, in particular to zero. The phase can be adjusted or regulated, for example, by modifying the length of the first and/or of the second light path.

For example, a phase adjusting means can be present for adjusting the phase of the train of first illuminating light pulses relative to the train of second illuminating light pulses. In particular, a first means for adjusting the length of the first light path can be arranged in the first light path as part of such a phase adjusting means. Alternatively or additionally, at least one second means for adjusting the length of the second light path can also be arranged in the second light path.

A very particularly advantageous embodiment of the apparatus according to the present invention comprises a control loop for regulating the phase to a predetermined or predeterminable value. Provision can be made in particular that what is present is a control loop for regulating the phase which regulates the phase—in particular with respect to a common focal region in the sample—to zero.

In a simple embodiment of the method, a determination is made, on the basis of the detected signal that is obtained from the detected light emerging from the sample, as to whether a sufficient temporal superposition of the illuminating light pulses has been achieved. Alternatively or additionally, the degree of temporal superposition can also be ascertained with a suitable sensor, for example with a two-photon absorption detector. Provision can be made here in particular that one part of the illuminating light propagating in the common illumination beam path is spatially divided off and guided to the sensor. The temporal coincidence of the illuminating light pulses can thus be checked and monitored parasitically, i.e. even during a sample investigation.

Both the sensor and the phase adjusting means can advantageously be constituents of the aforementioned control loop. Provision can also be made, in particular, that an electronic regulating system, which receives signals from the sensor and outputs positioning signals to the phase adjusting means, is a constituent of the control loop.

In particular in order to carry out a sample investigation by means of coherent Raman spectroscopy and/or in order to generate a Raman image, in particular an SRS image, of at least a part of a microscopic sample, for example the first illuminating light bundle can function as a Stokes illuminating light bundle and the second illuminating light bundle as a pump illuminating light bundle. Alternatively, it is also possible for the second illuminating light bundle to function as a Stokes illuminating light bundle and the first illuminating light bundle as a pump illuminating light bundle.

A particularly reliable and accurate sample investigation is possible in this context, in particular, if the linear polarization of the second illuminating light bundle is switched over at a frequency in the range from 10 to 30 MHz, in particular in the range from 10 MHz to 20 MHz, in particular of 20 MHz. It can be advantageous in particular if the linear polarization of the second illuminating light bundle is switched over at a frequency that is lower than a pulse repetition frequency of the first and/or of the second illuminating light bundle.

As already mentioned, a module can advantageously make possible in simple fashion the manufacture, optionally also at a later date, of an apparatus according to the present invention. The module is preferably embodied in such a way that it can be arranged in the beam path of a microscope, in particular of a confocal scanning microscope; the module can comprise alignment means for aligning the module relative to the other components of the microscope. Preferably the optical components of the module are prealigned, so that only the module as a whole needs to be aligned relative to the beam path of a microscope.

In a particular embodiment the module comprises a polarizing beam splitter that defines the beginning of a first and of a second light path. As already described earlier, a primary illuminating light bundle can be spatially divided with the polarizing beam splitter as a function of linear polarization, and the portions having different linear polarizations can be directed separately from one another into the first and second light path. An acousto-optic component is also provided, which combines the first and the second light path again so as to make possible a spatial overlapping of the illuminating light bundles and their portions in the sample.

In a very particularly advantageous embodiment the module contains in the first light path a first means for adjusting the length of the first light path, and/or in the second light path at least one second means for adjusting the length of the second light path. With the aid of at least one of these means, the phase of a pulse train propagating along the first light path can be adjusted relative to a pulse train propagating along the second light path.

The module can in particular also comprise an (in particular, electronic) regulating apparatus for regulating the phase of a pulse train propagating in the first light path relative to a pulse train propagating in the second light path.

The module can advantageously also comprise a sensor, for example a two-photon absorption detector, with which the degree of temporal superposition of first illuminating light pulses that propagate along the first light path and second illuminating light pulses that propagate along the second light path is ascertained.

Figure 2:
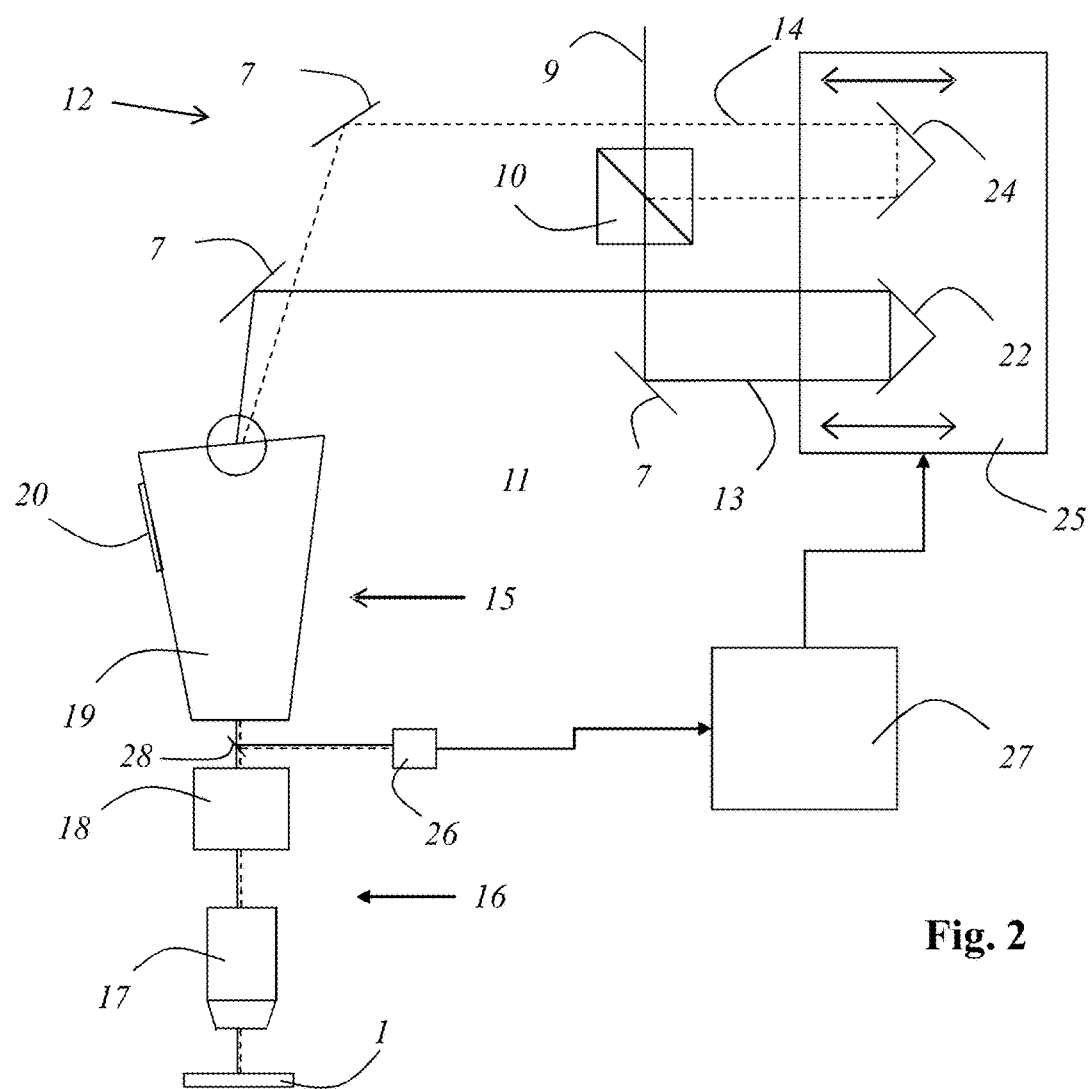

The subject matter of the invention is schematically depicted in the drawings and will be described below with reference to the Figures, identically functioning elements being labeled with the same reference characters. In the drawings:

FIG. 1 schematically shows an exemplifying embodiment of an apparatus according to the present invention embodied as a scanning microscope; and FIG. 2 schematically shows an exemplifying embodiment of an apparatus according to the present invention having a control circuit.

FIG. 1 schematically shows an exemplifying embodiment of an apparatus according to the present invention, embodied as a scanning microscope, for investigating a sample 1. In the interest of better clarity, however, only the illumination of the sample is depicted, but not the detected light emerging from the sample and the detection thereof.

The scanning microscope comprises a first light source 2 that generates a first, pulsed illuminating light bundle 3 having a first linear polarization direction. The scanning microscope furthermore comprises a second light source 4 that generates a second, pulsed illuminating light bundle 5 whose linear polarization direction is continuously switched over by a switchover apparatus 6, in particular an acousto-optic or electro-optic modulator, between a first linear polarization direction and a second linear polarization direction different from the first linear polarization direction.

Second illuminating light bundle 5, after deflection with a deflection mirror 7, is combined with the aid of a beam combiner 8 with first illuminating light bundle 3 to yield a primary illuminating light bundle 9.

Primary illuminating light bundle 9 is then spatially divided with a polarizing beam splitter 10 as a function of linear polarization, and portions 13, 14 having different linear polarizations are directed separately from one another into a first light path 11 and a second light path 12. First portion 13 having the first linear polarization direction propagates along first light path 11, while second portion 14 having the second linear polarization direction propagates along second light path 12.

The scanning microscope comprises an acousto-optic component 15 that combines light paths 11, 12 so that first portion 13 having the first linear polarization direction, collinearly combined with second portion 14 having the second linear polarization direction, travels into a common illumination beam path 16 for illumination of sample 1. Located in illumination beam path 16 is an objective 17 that focuses the illuminating light onto or into sample 1, and a beam deflection device 18 for guiding the focus of the illuminating light over or through sample 1.

Acousto-optic component 15 is embodied as an acousto-optic tunable filter (AOTF) and comprises an optical crystal 19 on which a piezo acoustic generator 20 is arranged. Piezo acoustic generator 20 is impinged upon by three different electrical HF frequencies and generates three mechanical waves that differ in terms of their frequency, namely a first, a second, and a third mechanical wave, which propagate simultaneously through crystal 19; this is not depicted in the Figure.

The frequency of the first mechanical wave is selected so that first illuminating light bundle 3 is diffracted at it and is thereby directed into the illumination beam path for illumination of sample 1. The frequency of the second mechanical wave is selected so that second illuminating light bundle 5 is diffracted at it and is thereby directed into the illumination beam path for illumination of sample 1 if said bundle has the first linear polarization direction. The frequency of the third mechanical wave is selected so that second illuminating light bundle 5 is diffracted at it and is thereby directed into the illumination beam path for illumination of sample 1 if said bundle has the second linear polarization direction.

In addition to some deflecting mirrors 7 that serve merely for beam guidance, a first means 21 for adjusting the length of first light path 11 is arranged in first light path 11. First means 21 for adjusting the length of first light path 11 comprises a first, angled double mirror 22 that is mounted displaceably on a displacement stage (not depicted). The length of first light path 11 can be modified by displacement of first double mirror 22. Also arranged in second light path 12, except for a deflecting mirror 7 that serves merely for beam guidance, is a second means 23 for adjusting the length of second light path 12. Second means 23 for adjusting the length of second light path 12 comprises a second, angled double mirror 24 that is mounted displaceably on a displacement stage (not depicted). The length of second light path 12 can be modified by displacement of second double mirror 24.

Means 21, 23 are constituents of a phase adjusting means 25 for adjusting the phase of the train of first illuminating light pulses of first portion 13 propagating along first light path 11, relative to the train of second illuminating light pulses of second portion 14 propagating along second light path 12.

FIG. 2 schematically shows an exemplifying embodiment of an apparatus according to the present invention having a control circuit for regulating the phase of the train of first illuminating light pulses of first portion 13 propagating along first light path 11, relative to the train of second illuminating light pulses of second portion 14 propagating along second light path 12.

The control loop comprises a sensor 26 that ascertains the degree of temporal superposition of the first and the second illuminating light pulses and is preferably embodied as a two-photon absorption detector. With the aid of a beam splitter 28, a part of the illuminating light combined by acousto-optic component 15 is divided off and delivered to sensor 26. The sensor conveys electrical signals, constituting an actual value of the measured phase, to an electronic regulating system 27 which outputs a control output to phase adjusting means 25 in consideration of the sensor signals, in such a way that the desired phase, preferably a phase of zero, is established as a result.

The invention has been described with reference to a particular embodiment, the same reference characters being used in most cases for identical or identically functioning components. It is self-evident, however, that modifications and variations can be carried out without thereby departing from the range of protection of the claims hereinafter.

The invention claimed is:

1. A method for investigating a sample, the sample being impinged upon by illuminating light, and detected light emerging from the sample being directed to a detector, and the illuminating light being directed through an acousto-optic component with which the impingement upon the sample by illuminating light is temporarily interrupted, wherein the sample is illuminated with a first illuminating light bundle that has a first linear polarization direction, and with a second illuminating light bundle whose linear polarization direction is continuously switched over between the first linear polarization direction and a second linear polarization direction different from the first linear polarization direction, the illuminating light having the first linear polarization direction proceeding along a first light path, the illuminating light having the second linear polarization direction proceeding along a second light path, and the acousto-optic component combining the first light path and the second light path so that the illuminating light having the first linear polarization direction, combined collinearly with the illuminating light having the second linear polarization direction, travels into a common illumination beam path for illumination of the sample.

2. The method according to claim 1, wherein at least one mechanical wave, at which at least one of the illuminating light bundles is diffracted and is thereby directed into the illumination beam path for illumination of the sample, propagates in the acousto-optic component.

3. The method according to claim 1, wherein
   a. a first mechanical wave, whose frequency is selected so that the first illuminating light bundle is diffracted at it and is thereby directed into the illuminating light beam path for illumination of the sample, propagates in the acousto-optic component; or
   b. a second mechanical wave, whose frequency is selected so that the second illuminating light bundle is diffracted at it and is thereby directed into the illuminating light beam path for illumination of the sample if said bundle has the first linear polarization direction, propagates in the acousto-optic component; or
   c. a third mechanical wave, whose frequency is selected so that the second illuminating light bundle is diffracted at it and is thereby directed into the illumination beam path for illumination of the sample if said bundle has the second linear polarization direction, propagates in the acousto-optic component.

4. The method according to claim 1, wherein the acousto-optic component comprises at least one acousto-optic tunable filter (AOTF) in which the mechanical wave or mechanical waves propagate.

5. The method according to claim 1, wherein a primary illuminating light bundle, which contains at least one of the first illuminating light bundle and the second illuminating light bundle in collinearly combined fashion, is spatially divided as a function of linear polarization, and the portions having different linear polarizations are directed separately from one another into the first and second light path.

6. The method according to claim 1, wherein
   a. at least a partial region of the sample is scanned with the first illuminating light bundle and with the second illuminating light bundle; or
   b. the foci of the first illuminating light bundle and of the second illuminating light bundle are moved, with the aid of a beam deflection device, over or through the sample, and in that context the detected light emerging from the sample is detected.

7. The method according to claim 1, wherein
   a. the impingement upon a sample by at least one of the first illuminating light bundle and by the second illuminating light bundle is temporarily interrupted with the acousto-optic component; or
   b. the impingement upon a sample by at least one of the first illuminating light bundle and by the second illuminating light bundle is interrupted with the acousto-optic component, if at least one of the first illuminating light bundle and the second illuminating light bundle would illuminate a region of the sample that is located outside a region to be investigated; or
   c. the impingement upon a sample by at least one of the first illuminating light bundle and the second illuminating light bundle is interrupted with the acousto-optic component, in the turnaround regions of a meander-shaped scan or on the return paths.

8. The method according to claim 1, wherein the light power level of at least one of the first and the second illuminating light bundle is adjusted or regulated with the acousto-optic component.

9. The method according to claim 1, wherein
   a. at least one of the first illuminating light bundle and the second illuminating light bundle are pulsed; or
   b. the first illuminating light bundle and the second illuminating light bundle are pulsed at the same pulse repetition frequency; or
   c. the pulse repetition frequency of the first illuminating light bundle or the pulse repetition frequency of the second illuminating light bundle is in the range from 40 MHz to 100 MHz or is 80 MHz.

10. The method according to claim 1, wherein the illuminating light having the first linear polarization direction, which proceeds along the first light path, comprises a train of first illuminating light pulses; and the illuminating light having the second linear polarization direction, which proceeds along the second light path, comprises a train of second illuminating light pulses,
    a. the phase of the train of first illuminating light pulses relative to the train of second illuminating light pulses being adjusted or regulated; or
    b. the phase of the train of first illuminating light pulses relative to the train of second illuminating light pulses being adjusted or regulated to zero.

11. The method according to claim 10, wherein
    a. the phase is adjusted or regulated by modifying the length of at least one of the first and the second light path; or
    b. a first means for adjusting the length of the first light path is arranged in the first light path; or at least one second means for adjusting the length of the second light path is arranged in the second light path, the first means or the second means being part of a control loop for regulating the phase.

12. The method according to claim 10, wherein
    a. the phase is sensed with the aid of a sensor or with the aid of a two-photon absorption detector, that receives at least a part of the combined illuminating light; or
    b. the phase is sensed with the aid of a sensor that is part of a control loop for regulating the phase.

13. The method according to claim 1, wherein
    a. the linear polarization of the second illuminating light bundle is switched over at a frequency in the range from 10 to 30 MHz or in the range from 10 MHz to 20 MHz or of 20 MHz; or
    b. the linear polarization of the second illuminating light bundle is switched over at a frequency that is lower than a pulse repetition frequency of at least one of the first and the second illuminating light bundle.

14. The method according to claim 1, wherein
    a. the first illuminating light bundle is used as a Stokes illuminating light bundle and the second illuminating light bundle as a pump illuminating light bundle, in order to carry out a sample investigation by means of coherent Raman spectroscopy or in order to generate a Raman image or an SRS image, of at least a part of a microscopic sample; or
    b. the second illuminating light bundle is used as a Stokes illuminating light bundle and the first illuminating light bundle as a pump illuminating light bundle, in order to carry out a sample investigation by means of coherent Raman spectroscopy or in order to generate a Raman image or an SRS image, of at least a part of a microscopic sample.

15. An apparatus or a scanning microscope for carrying out a method according to claim 1.

16. An apparatus or a scanning microscope or a confocal scanning microscope for investigating a sample, the sample being impinged upon by illuminating light, and detected light emerging from the sample being directed to a detector, and the illuminating light being directed through an acousto-optic component with which the impingement upon the sample by illuminating light is temporarily interrupted, wherein the illuminating light comprises a first illuminating light bundle having a first linear polarization direction, and comprises a second illuminating light bundle whose linear polarization direction is continuously switched over by a switchover apparatus or by an acousto-optic or electro-optic modulator between the first linear polarization direction and a second linear polarization direction different from the first linear polarization direction, the illuminating light having the first linear polarization direction proceeding along a first light path and the illuminating light having the second linear polarization direction proceeding along a second light path, and the acousto-optic component combining the light paths so that the illuminating light having the first linear polarization direction, combined collinearly with the illuminating light having the second linear polarization direction, travels into a common illumination beam path for illumination of the sample.

17. The apparatus according to claim 16, wherein at least one mechanical wave, at which at least one of the illuminating light bundles is diffracted and is thereby directed into the illumination beam path for illumination of the sample, propagates in the acousto-optic component.

18. The apparatus according to claim 16, wherein
 a. a first mechanical wave, whose frequency is selected so that the first illuminating light bundle is diffracted at it and is thereby directed into the illuminating light beam path for illumination of the sample, propagates in the acousto-optic component; or
 b. a second mechanical wave, whose frequency is selected so that the second illuminating light bundle is diffracted at it and is thereby directed into the illuminating light beam path for illumination of the sample if said bundle has the first linear polarization direction, propagates in the acousto-optic component; or
 c. a third mechanical wave, whose frequency is selected so that the second illuminating light bundle is diffracted at it and is thereby directed into the illumination beam path for illumination of the sample if said bundle has the second linear polarization direction, propagates in the acousto-optic component.

19. The apparatus according to claim 16, wherein the acousto-optic component comprises at least one acousto-optic tunable filter (AOTF) in which the mechanical wave or mechanical waves propagate.

20. The apparatus according to claim 16, wherein at least one primary light source is present which generates a primary illuminating light bundle that contains at least one of the first illuminating light bundle and the second illuminating light bundle; and a polarizing beam splitter spatially divides the primary illumination light bundle as a function of linear polarization and directs the portions having different linear polarizations separately from one another into the first and second light path.

21. The apparatus according to claim 16, wherein
 a. a beam deflection device is present which deflects at least one of the first illuminating light bundle and the second illuminating light bundle for scanning of a sample; or
 b. a beam deflection device moves the foci of the first illuminating light bundle and of the second illuminating light bundle over or through the sample, and in that context the detected light emerging from the sample is detected.

22. The apparatus according to claim 16, wherein
 a. the acousto-optic component interrupts at least one of the first illuminating light bundle and the second illuminating light bundle, if a sample is not to be impinged upon by illuminating light; or
 b. the acousto-optic component interrupts at least one of the first illuminating light bundle and the second illuminating light bundle, if at least one of the first illuminating light bundle and the second illuminating light bundle would illuminate a region of the sample that is located outside an region to be investigated; or
 c. the acousto-optic component interrupts the impingement upon a sample by at least one of the first illuminating light bundle and the second illuminating light bundle in the turnaround regions of a meander-shaped scan or on the return paths.

23. The apparatus according to claim 16, wherein the light power level of at least one of the first and of the second illuminating light bundle is adjustable or regulatable with the acousto-optic component.

24. The apparatus according to claim 16, wherein
 a. at least one of the first illuminating light bundle and the second illuminating light bundle are pulsed; or
 b. the first illuminating light bundle and the second illuminating light bundle are pulsed at the same pulse repetition frequency; or
 c. the pulse repetition frequency of the first illuminating light bundle or the pulse repetition frequency of the second illuminating light bundle is in the range from 40 MHz to 100 MHz or is 80 MHz.

25. The apparatus according to claim 16, wherein the illuminating light having the first linear polarization direction, which proceeds along the first light path, comprises a train of first illuminating light pulses; and the illuminating light having the second linear polarization direction, which proceeds along the second light path, comprises a train of second illuminating light pulses,
 a. the phase of the train of first illuminating light pulses relative to the train of second illuminating light pulses being adjustable or regulatable with a phase adjusting means; or
 b. the phase of the train of first illuminating light pulses relative to the train of second illuminating light pulses being adjusted or regulated to zero.

26. The apparatus according to claim 25, wherein as part of the phase adjusting means, a first means for adjusting the length of the first light path is arranged in the first light path, or at least one second means for adjusting the length of the second light path is arranged in the second light path.

27. The apparatus according to claim 25, wherein
 a. a control loop for regulating the phase to a predetermined or predeterminable value is present; or
 b. a control loop for regulating the phase, which regulates the phase to zero, is present.

28. The apparatus according to claim 27, wherein
 a. a sensor or a two-photon absorption detector, that receives at least a part of the combined illuminating light, is a constituent of the control loop; or
 b. the phase adjusting means is a constituent of the control loop; or
 c. an electronic regulating system, which receives signals from the sensor and outputs positioning signals to the phase adjusting means, is a constituent of the control loop.

29. The apparatus according to claim 16, wherein
a. the linear polarization of the second illuminating light bundle is switched over at a frequency in the range from 10 to 30 MHz or in the range from 10 MHz to 20 MHz or of 20 MHz; or
b. the linear polarization of the second illuminating light bundle is switched over at a frequency that is lower than a pulse repetition frequency of at least one of the first and the second illuminating light bundle.

30. The apparatus according to claim 16, wherein
a. the first illuminating light bundle functions as a Stokes illuminating light bundle and the second illuminating light bundle as a pump illuminating light bundle, in order to carry out a sample investigation by means of coherent Raman spectroscopy or in order to generate a Raman image of at least a part of a microscopic sample; or
b. the second illuminating light bundle functions as a Stokes illuminating light bundle and the first illuminating light bundle as a pump illuminating light bundle, in order to carry out a sample investigation by means of coherent Raman spectroscopy or in order to generate a Raman image of at least a part of a microscopic sample.

31. A module for manufacturing an apparatus according to claim 16, wherein the module comprises a polarizing beam splitter that defines the beginning of a first and of a second light path, and comprises an acousto-optic component that combines the first and the second light path.

32. The module according to claim 31, wherein
a. a first means for adjusting the length of the first light path is arranged in the first light path, or at least one second means for adjusting the length of the second light path is arranged in the second light path; or
b. a regulating apparatus for regulating the phase of a pulse train propagating in the first light path relative to a pulse train propagating in the second light path is present.

33. The module according to claim 31, wherein the module comprises a sensor, for example a two-photon absorption detector, for ascertaining the degree of temporal superposition of first illuminating light pulses that propagate along the first light path and second illuminating light pulses that propagate along the second light path.

* * * * *